United States Patent [19]

Razim et al.

[11] 4,042,427
[45] Aug. 16, 1977

[54] PROCESS FOR CONTROLLING FUSED SALT NITRIDATION OF METALS WITH A SOLID ELECTROLYTE ELECTRODE

[75] Inventors: Claus Razim; Csaba Lovasz, both of Stuttgart; Kurt Baier, Fellbach, all of Germany

[73] Assignee: Daimler-Benz Aktiengesellschaft, Germany

[21] Appl. No.: 560,822

[22] Filed: Mar. 21, 1975

[30] Foreign Application Priority Data

Mar. 21, 1974 Germany .............................. 2413643

[51] Int. Cl.² ................................................ C21D 1/48
[52] U.S. Cl. ..................................... 148/15.5; 148/20; 148/27
[58] Field of Search ........................... 148/15.5, 27, 20; 204/195 S

[56] References Cited

U.S. PATENT DOCUMENTS

| | | | |
|---|---|---|---|
| 2,568,860 | 9/1951 | Leininger et al. | 148/15.5 |
| 3,022,204 | 2/1962 | Muller et al. | 148/15.5 |
| 3,726,772 | 4/1973 | Takahashi et al. | 148/15.5 |
| 3,752,753 | 8/1973 | Fitterer | 204/195 S |
| 3,912,547 | 10/1975 | Gaucher et al. | 148/15.5 |

Primary Examiner—Walter R. Satterfield
Attorney, Agent, or Firm—Craig & Antonelli

[57] ABSTRACT

A process for controlling the nitriding effect of a nitriding bath of a salt melt containing alkali cyanate for the nitridation of iron and iron alloys wherein the nitriding effect of the bath is maintained in a specific range by determining the voltage occurring at an electrode of a solid electrolyte which conducts oxygen ions immersed in the nitriding bath.

15 Claims, 4 Drawing Figures

PROCESS FOR CONTROLLING FUSED SALT NITRIDATION OF METALS WITH A SOLID ELECTROLYTE ELECTRODE

This invention relates to a process for the nitridation of metals, especially iron and iron alloys, in alkali cyanate salt baths which contain an alkali cyanide and which preferably are free of an alkali cyanide, wherein the nitriding effect can be maintained in the optimum range by the use of chemical and/or electrochemical measures.

It is known to nitride workpieces of iron and iron alloys by dipping the workpieces into a salt bath at temperatures of between 500° and 600° C., the salt bath containing alkali cyanide and alkali cyanate. Such baths are operated in practice with cyanate contents of between 20 and 40%, calculated as KOCN and with cyanide contents of between 30 and 60%, calculated as NaCN. The remainder of the baths consists of alkali carbonate which is formed automatically by oxidation during the operation of the baths. Such baths can furthermore contain alkali (i.e. alkali metal) and alkaline earth chlorides to save some of the cyanide and cyanate salts or to reduce the fusion point of the melt.

In this process, the nitridation can be conducted with or without aeration of the bath; a considerable increase in the nitriding effect is attained by passing air or other gases with oxidizing activity in a fine distribution through the bath.

It is also conventional to obtain, by using the anodic polarization of the metal workpieces, especially workpieces of iron and iron alloys, a substantial improvement in the adhesive strength of the bonding zones during treatment in salt baths containing alkali cyanide and alkali cyanate at temperatures between about 500°–600° C. The desired effect is achieved to a maximum degree if the workpieces are polarized with high current density only at the beginning of the nitridation step and are then treated without or only with minor current density during the remainder of the nitridation operation.

It is furthermore known that the formation of porous or dual nitridation zones with reduced sealing capacity can be avoided by maintaining the iron content of the bath at a low level with the use of a suitable lining for the bath vessel; this means, therefore, that iron vessels can be utilized only if they are lined with metals which are not dissolved in the salt bath containing the cyanide and the cyanate salts, i.e. such metals as Al, Ti, V, Zr, W, Co, Ni, or Cr.

It is also known that thicker nitridation layers can be obtained with the aid of an auxiliary electrode in a salt melt containing alkali cyanide and alkali cyanate, with the simultaneous electrolysis of this salt melt; in this process, the auxiliary electrode is connected as the anode, and the crucible containing the bath is connected as the cathode.

Finally, it is conventional to regulate nitriding baths containing cyanide and cyanate in their nitridation activity by the addition of alkali and/or alkaline earth cyanamides and by keeping the baths in this way at the upper limit of their operating capacity.

The objective of the present invention is to provide a simple and effective process for the nitridation of metals, particularly alloyed and unalloyed steels, with or without the addition of alkali and/or alkaline earth chlorides, wherein the nitriding effect of the bath can be controlled and thus can always be maintained at an optimum, as well as to provide a cyanide-free bath for this purpose as a preferred means for conducting the present process.

This objective is attained by determining the nitriding effect of the salt melt with the aid of the voltage of a solid electrolyte immersed in the nitriding bath and capable of conducting oxygen ions, and maintaining this nitriding effect at a desired value.

It is known that solid electrolytes which conduct oxygen ions and consist, for example, of 85% by weight of $ZrO_2$ and 15% by weight of CaO as the binder, and which, as unilaterally closed tubes, are contacted on the inside and outside with platinum, can be utilized for measuring the oxygen activity (fugacity) of gas mixtures (see: H. H. Moebius, Z. Phys. Chem 230, 396 [1964]).

However, it has been found surprisingly that there is an intimate correlation between the nitriding effect of a cyanate-containing salt melt and the measurable voltage at an aforementioned solid electrolyte conducting oxygen ions, which is immersed in the melt. Thus, for example, a solid electrolyte conducting oxygen ion, which consists of $Pt/Zr_{0.85}Ca_{0.15}O_{1.85}/Pt$, yields well measurable voltages of between 0.6 and 1.2 volts in salt melts containing alkali cyanide and/or cyanate salts with the aid of a high-ohmic voltameter.

By measuring this potential and by the use of measures to maintain this potential in an optimum range, previously determinable by a few routine experiments, for the material to be nitrided, it is possible to attain a simple regulation and control of the nitriding effect.

Thus, it has been found that an optimum nitride layer is formed only in those cyanate-containing salt melts between 500° and 650° C., preferably between 570° and 590° C., wherein the potential of the immersed solid electrolyte ranges between about 0.7 and about 1.1 volts, preferably between 0.9 and 1.0 volt. The composition of the melt, such as, for example, its cyanide and carbonate content and also the presence of larger proportions of alkali and alkaline earth chlorides, is only of secondary importance. It is only necessary, as will be explained further below, for the composition to be such that the above-mentioned optimum potential is obtained at the oxygen-ion-conducting solid electrolyte.

Since the use of cyanide-containing melts is disadvantageous because of their toxicity, a preferred agent for conducting the process of this invention is a cyanide-free melt consisting, under practical conditions of 60–100% by weight of alkali cyanate, calculated as KOCN, and 0–40% by weight of alkali and/or alkaline earth chlorides, calculated as NaCl. The remainder, if any, consists of undesired by-products of technically pure substances and of alkali carbonate produced automatically due to oxidation during the operation of the baths. The nitriding effect of such a cyanide-free bath can be satisfactorily controlled according to the process of this invention.

The unavoidable decomposition of the cyanate takes place, in the salt melt preferably employed according to this invention, with the formation of carbonate; whereas poisonous cyanide is formed only in negligible amounts. Due to the formation of decomposition products and due to the production of minor amounts of $(Fe(CN)_6)^{4-}$ from dissolved iron, the potential at the immersed solid electrolyte is altered undesirably.

However, it has furthermore been found that this salt melt can be regulated to be within the desired potential, i.e. from about 0.7 to about 1.1 volts range, by means of chemical additives. A drop of potential at the solid electrolyte can be prevented by adding inorganic salts of elements of groups IIA and IIB, especially alkaline earth chlorides and $ZnCl_2$, which are soluble in the bath. A rise in potential at the solid electrolyte can be prevented by adding metallic oxides, such as iron oxide, chromium oxide, manganese oxide, or sodium oxide or alkali and/or alkaline earth cyanamides, wherein cyanamides and iron oxide are preferred. The introduction of aid or other oxidizing gases is likewise a preferred measure for preventing a rise in potential at the solid electrolyte and is carried out between two operating steps, e.g. overnight.

Accordingly, a chemical control of the bath can be effected on the basis of the indicated potential of a solid electrolyte which conducts oxygen ions, by influencing the alkalinity or acidity of the salt melt; namely, the reaction $CNO^- \rightarrow CN^- + O$, or by generally introducing, in a manner known to a chemist, additives into the bath which chemically react with the bath components at the operating temperature of between 500° and 650° C. to adjust the potential. As will be demonstrated hereinbelow, it is also possible to take electrochemical measures for this purpose.

The extraordinary useful employment of the solid electrolytes which conduct oxygen atoms permits a satisfactory control of the nitriding effect which, however, is discontinuous under certain circumstances. Thus, for example, air or gases having an oxidizing effect are not to be utilized during the nitriding process proper.

Since, however, a continuous regulation and control of the nitriding process is frequently desired, the fact is exploited that—as has furthermore been found—the workpieces to be nitrided possess a certain electric potential, depending on the aging condition of the bath, with respect to various immersed metals. The optimum nitriding effect of the salt melt can be characterized by a potential interval or difference measured between the workpiece and, for example, a silver rod. If the potential of the workpiece with respect to the selected metal changes, the desired value can be electronically regulated by the use of an external voltage between the workpiece and the vessel containing the bath. It has been found that this external voltage is not to exceed a value of about 1,050 millivolts, since otherwise a scaly surface is produced on the workpiece. If a higher external voltage than 1,050 mV were required to attain the desired voltage of the solid electrolyte, the bath could be regulated in the desired manner by means of chemical additives, again in dependence on the indicated potential potential of the solid electrolyte. The currents occurring during this type of polarization of the workpiece surface are unimportant for the nitriding effect of the bath.

The possibility of a continuous control of the nitriding effect by an electronic controller by way of the potential of a metal electrode as the control voltage requires, however, auxiliary devices.

It has furthermore been found, though that there still flows a sufficiently high current between a workpiece and a metal piece immersed in the melt for maintaining a potential. The magnitude of the potential is then different from one metal to the next and depends to a minor extent on the temperature; however, this can be determined by a few routine experiments. This potential, exploiting the high temperature of the bath as an energy source, now offers the most advantageous and least expensive improvement in the control of the nitriding effect on the workpieces according to the present invention. The use of various metal plates, e.g., Ni, Co or Ti in conductive connection with the workpieces, wherein both the plates and the workpieces are suspended so that they are insulated from the vessel containing the salt melt, depends on the aging condition of the bath which requires from time to time the aforementioned chemical regulation and, due to discharged substance, also refilling if necessary.

The preferred refilling salt consists of a salt mixture containing more than 60% by weight of alkali cyanate, with the remainder being alkali and/or alkaline earth chlorides, or it consists only of pure alkali cyanate.

However, it has furthermore been discovered that the use of an auxiliary electrode immersed in the melt, to which a voltage is applied with respect to the bath vessel, can change the voltage of the immersed solid electrolyte to be measured. Depending on the aging condition of the bath, a voltage of a certain direction can be selected which keeps the nitriding effect of the melt in the optimum range. This bath control method is distinguished by the advantage that baths which would otherwise be unsuitable for the nitridation can continue to be used.

Accordingly, the utilization of the solid electrolytes which conduct oxygen ions, as conventional for measuring the oxygen activity of gas mixtures, for controlling the nitriding effect of a nitriding bath offers the possibility of maintaining the bath at a desired optimum of its nitriding effect and of keeping up the control of the bath by chemical and/or electrochemical measures.

For example, it was found that with the use of a silver rod as the reference electrode a voltage of $-100$ to $+50$ mV is to be maintained between this rod and the workpiece, which value can be set by regulating the external voltage between the workpiece and the crucible.

However, the process of this invention does not only permit the achievement of optimum nitridation layers, but also provides the advantages that the nitriding period is reduced by almost one-third, that inexpensive iron crucibles can be employed without the necessity of lining such crucibles with materials insoluble in the salt melt, that the bath need not be aerated during the nitridation step, and furthermore that a nonpoisonous, cyanide-free salt bath can be used. Therefore, the special precautionary measures can be eliminated which must be observed in cyanide-containing baths when working with the melt and when discharging the salt residues and the waste water.

Experiments conducted with nitriding baths of KOCN, 90% KOCN + 10% NaCl, as well as 66% KOCN + 34% NaCl on steels at a temperature of 570° to 590° C. over time periods up to 192 hours showed that the nitriding effect can be set and the thus-adjusted value can be maintained practically constant in accordance with the control process of this invention.

Two embodiments of this invention will be further understood from the following description and the accompanying drawings wherein.

Figure 1:
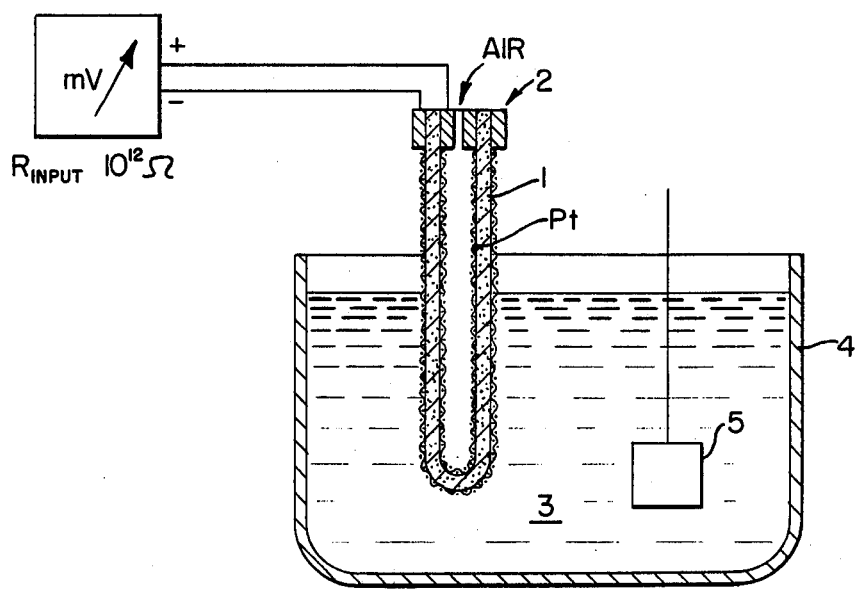
FIG. 1 is a schematic view of a typical nitriding apparatus wherein a solid electrolyte is used to determine the "nitriding effect"

FIG. 1 schematically illustrates an arrangement of the solid electrolyte 1 as it can be utilized as an electrode 2 in a nitriding bath 3 within a crucible 4. Workpiece 5 is immersed in the salt melt forming the bath. In our experiments the solid electrolyte (which is contacted on the inside and outside with platinum) used is the mixture of $ZrO_2$ with 3% CaO, obtained from the ZIRCONIUM CORPORATION OF AMERICA, Cleveland, Ohio. Analogously, the product of this firm with 7.5% yttrium oxide could also be used. Also the employment of other solid electrolytes which conduct oxygen ions is, of course, also possible, such as, for example $ThO_2$ or $Al_2O_3$ wherein, however, different voltage potentials would be expected. The measurable voltage (potential) on the oxygen-ion-conducting solid electrolyte used is dependent, in accordance with the Nernst equation, on the temperature. However, in the temperature range in question, e.g. 560°–580° C. such potential amounts to only a few millivolts.

The use of this solid electrolyte as an electrode is effected, in practice, always before the nitriding treatment, and thus a desired oxygen activity is obtained in the melt by means of the chemical additives. Of course, the solid electrolyte can also be utilized during the nitriding treatment, e.g. for the control of the process, or also, for a subsequent regulation of the oxygen activity, and can constantly remain in the bath.

Figure 2:
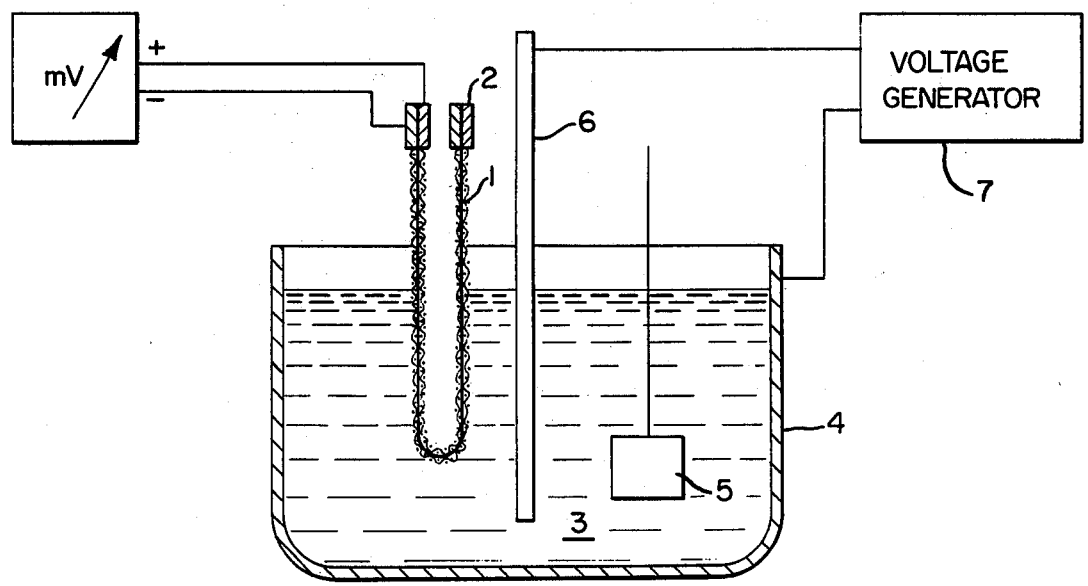
FIG. 2 is a schematic view showing a nitriding apparatus wherein a solid electrolyte is used together with an auxiliary electrode for applying an external control voltage.

FIG. 2 schematically illustrates use of Ag reference electrode 6 together with a control arrangement including voltage generator 7. In principle, also other metals could be used for the reference electrode, such as for example Ni, Co, V, Cu, Au, Pt, etc. (which proved to be not so suitable under practical conditions). The reason for this is that, in several metals, the voltage between the reference electrode and the workpiece cannot be made sufficiently reproducible, or that such metals are not feasible for reasons of cost.

The control voltage between the workpiece (negative) and the silver rod (positive) ranges—depending on the set oxygen activity of the melt, the degree of nitriding, and the alloy composition of the workpiece—between $-300$ and $+100$ mV (workpiece is in most cases negative). If this voltage, by means of an external voltage is controlled—depending on the aging condition of the bath—to assume a value of between $-100$ and $+50$ mV, the nitride layer growth is promoted and the pore formation in the iron nitride layer is greatly reduced. The magnitude of this external voltage, however, must nowise exceed approximately 1050 mV, and in salt melts of a high oxygen activity this value should not exceed 300-400 mV, since otherwise scaly layers are obtained. The external voltage is controlled with the aid of a customary millivolt meter; a higher input resistance is not necessary.

For controlling the bath temperature, the generally known electronic temperature governors for industrial purposes are employed which have, for example, a thermocouple as a measuring probe.

In our experiments, technically pure iron workpieces with 0.15% carbon content were used. Also alloyed steels, according to expectation, can also be satisfactorily nitrided. Only the "control voltage" to be set must have a slightly changed value ($\pm$ 0–30 mV), if layers with a low pore content are to be desired. Experience gained during practical operation shows that a bath composition of 89% KOCN (with approximately 1% KCN impurities), 10% NaCl, and 1% $CaCl_2$ yields almost optimum nitriding effects.

In one series of experiments with the embodiment shown in FIG. 2, the voltage to be set between the workpiece and the Ag reference electrode is selected during the course of 4 weeks to increase from $-100$ mV to $-25$ mV, in case the potential on the oxygen-ion-conducting solid electrolyte is about 930 mV. If the oxygen activity is higher (equivalent, for example, to 900mV), a lower value is set, e.g. instead of $-75$ mV (approximately tenth operating day) only $-80$ mV or even $-85$ mV. In case of lower active oxygen concentrations (equivalent, for example, to 960 mV) a higher value should be set e.g. instead of $-75$ mV already $-70$ mV or even $-65$ mV. The control voltage then results automatically and depends, on the "nitriding effect" or on the "nitrogen activity" of the melt.

In the nitriding treatment of alloys, a different voltage value can be preselected than in case of "C-15" workpieces. However, these values are in the range from $-150$ to $+50$ mV and differ only insubstantially over the otherwise customary voltage values for the "C-15" workpieces.

The voltage to be preselected is dependent in a first approximation on the carbonate content of the salt melt and shows the following correlation:

| emf - Workpiece - Ag | % by Wt. $K_2CO_3$ of the Melt |
| --- | --- |
| $-150$ mV | 2 |
| $-130$ mV | 4 |
| $-100$ mV | 8 |
| $-75$ mV | 12 |
| $-50$ mV | 16 |
| $-25$ mV | 20 |

A prerequisite for this is that the voltage measured at the solid electrolyte is approximately 920 mV and the crucible contains 500–700 kg. of melt.

The mode of operation in melts of a different composition does not differ from the above-mentioned case. One must merely take into account that other recipes do not ensure an optimum bath efficiency and that the "nitriding effect" thereof will fade earlier. However, other recipes make it possible, in practice, to produce special cases of surface layers, for example those with very porous or almost nonporous surfaces or with more or less deep nitrogen diffusion zones underneath the junction layer. These melts then contain either an extremely low quantity of cyanide and/or carbonate as impurities or they are purposely enriched in such impurities. Also other additives, such as, for example $CaCl_2$ or $Na_2N$-CN, are purposely employed for a certain layer formation.

Figure 3A:
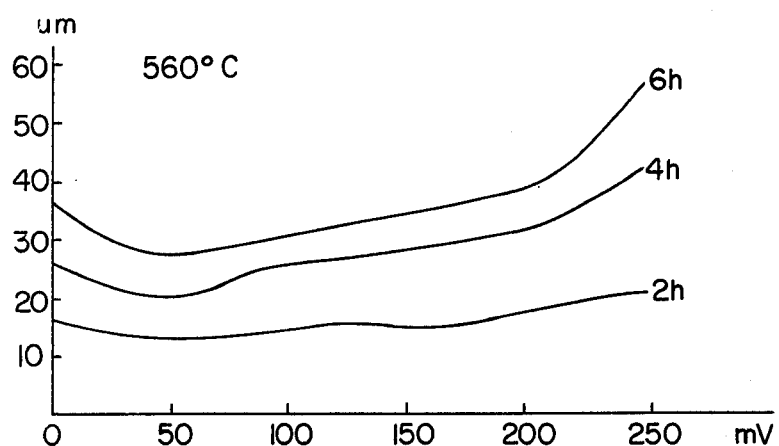
FIGS. 3A, 3B, and 3C are graphical representations showing the dependence of the layer thickness on the voltage employed and on the bath temperature in the nitriding process of the invention.
Figure 3B:
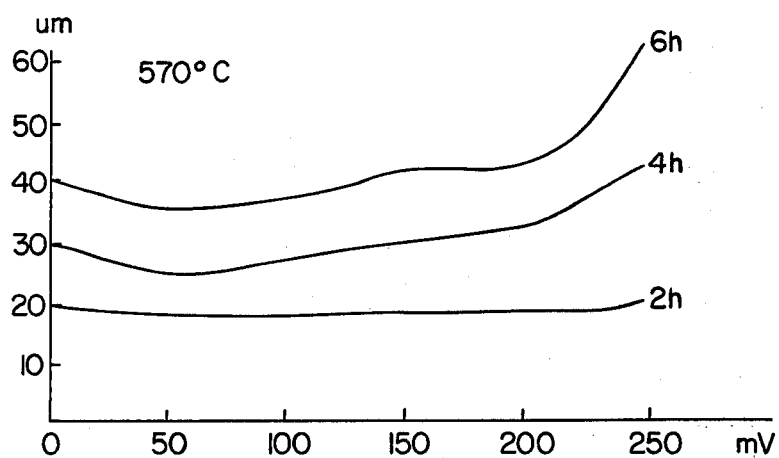
Figure 3C:
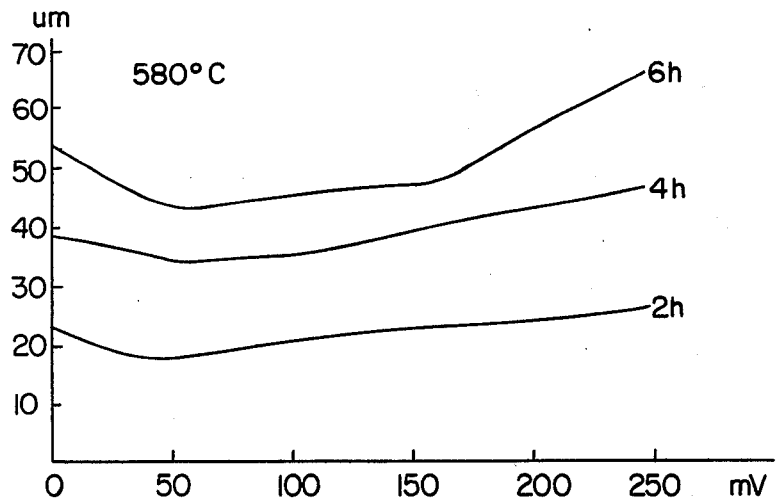

The nitride layer thickness of the junction zone is primarily a function of the treatment time and the bath temperature, see FIGS. 3A, 3B and 3C, in three illustrations, the dependence of the layer thickness on the voltage employed (external voltage const.) and on the bath temperature. It is to be noted that the individual curves are only average values.

The chemical additives introduced into the melt for the purpose of a chemical control of the bath are only those which are not deleterious to the environment and which are favorable from a financial viewpoint. Such additives are heretofore disclosed. Further possible additives, such as, for example, $MgCl_2$, borax, alkali carbonates and alkaline earth carbonates, phosphates are also usable on a large technical scale. The purposeful addition of, for example, cyanides and barium salts can only be effected to a limited extent in industry for reasons of environmental protection. The utilization of molybdates, vanadates, $ZnCl_2$, LiCl, or even the salts of rarer metals restricts the large-technical application for reasons of cost.

The chemical control, or the use of such additives, takes place only after testing the oxygen activity of the melt and—normally—before the nitriding treatment of the workpieces, possibly in exception cases also during such nitriding treatment. The amount of these additives which is introduced always depends on the voltage measured on the oxygen-ion-conducting solid electrolytes and also possibly on the chemical analysis of the respective melt. In practice, these are in amounts of between 0.1 and 5 kg., based on 500 kg. of melt (i.e. approximately 0.02 – 1.0%).

While the novel principles of the invention have been described, it will be understood that various omissions, modifications and changes in these principles may be made by one skilled in the art without departing from the spirit and scope of the invention.

What is claimed is:

1. A process for controlling the nitriding effect of a nitriding bath of a salt melt containing alkali cyanate, for the nitridation of iron and iron alloys, which comprises providing a nitriding bath comprising a salt melt, said salt melt consisting essentially of 60–100% by weight of alkali cyanate, calculated as KOCN, 0–40% by weight of alkali metal chloride, alkaline earth chloride or mixture of said chlorides, calculated as NaCl, and a balance comprised of by-products of the cyanate or chlorides and the decomposition products thereof, determining the voltage established on an electrode of an oxygen ion-conducting solid electrolyte immersed in said salt melt, said electrolyte being capable of yielding well measurable voltages in said salt melt, and adjusting the voltage established by said solid electrolyte to be within a range of between 0.7 and 1.1 volt at a temperature of the salt melt that is between 500° and 650° C.

2. A process according to claim 1, wherein at a temperature of the salt melt of between 570° and 590° C., the voltage of the solid electrolyte is maintained between 0.9 and 1.0 volts.

3. A process according to claim 1, wherein the indicated voltage of the oxygen-ion-conducting solid electrolyte is controlled by chemical additives to the salt melt.

4. A process according to claim 3, wherein additives are introduced which affect the alkalinity or the acidity of the salt melt.

5. A process according to claim 4, wherein a voltage drop at the solid electrolyte is prevented by the addition of alkaline earth chlorides and $ZnCl_2$.

6. A process according to claim 3, wherein a voltage rise at the solid electrolyte is prevented by the addition of alkali cyanamides, alkaline earth cyanamides, iron oxide or mixtures thereof.

7. A process according to claim 1, wherein the voltage set at the solid electrolyte is regulated by electrochemical measures.

8. A process according to claim 7, wherein the nitriding effect is regulated by means of a control voltage applied between a workpiece to be nitrided and a crucible containing said bath, said control voltage being regulated by the EMF between the workpiece and a metal piece additionally arranged in the bath.

9. A process according to claim 8, wherein the metal piece is a silver rod.

10. A process according to claim 7, wherein depending on the aging condition of the bath, various metal plates are used outside the bath, said plates being metallically and conductively connected to the workpiece to be nitrided.

11. A process according to claim 1, wherein said solid electrolyte is a mixture of $ZrO_2$ with 3% CaO which is surrounded by platinum.

12. A process according to claim 11, wherein said salt melt consists essentially of 89% KOCN containing approximately 1% KCN, 10% NaCl, and 1% $CaCl_2$.

13. A process according to claim 3, wherein the amount of chemical additives added to said salt melt is 0.02 to 1.0%.

14. A process according to claim 9, wherein the EMF between the workpiece and the silver rod is from −100 to +50 mV and the magnitude of the voltage applied between the workpiece and a crucible containing the bath does not exceed 1050mV.

15. A process according to claim 1, wherein the solid electrolyte is a mixture of $ZrO_2$ with 7.5% yttrium oxide surrounded by platinum.

* * * * *